United States Patent
Dastidar et al.

(10) Patent No.: US 7,220,435 B2
(45) Date of Patent: May 22, 2007

(54) PROCESS FOR THE PRODUCTION OF GLYCINE ENRICHED NACI CRYSTALS WITH IMPROVED FLOW

(75) Inventors: Parthasarathi Dastidar, Gujarat (IN); Pushpito Kumar Ghosh, Gujarat (IN); Amar Ballabh, Gujarat (IN); Darshak Rameshbhai Trivedi, Gujarat (IN); Amitava Pramanik, Mumbai (IN); Velayudhan Nair Gopa Kumar, Mumbai (IN)

(73) Assignees: Council of Scientific & Industrial Research, New Delhi (IN); Hindustan Lever Limited, Maharashhtra (IN)

( * ) Notice: Subject to any disclaimer, the term of this patent is extended or adjusted under 35 U.S.C. 154(b) by 502 days.

(21) Appl. No.: 10/745,758

(22) Filed: Dec. 23, 2003

(65) Prior Publication Data

US 2005/0136131 A1 Jun. 23, 2005

(51) Int. Cl.
*A61K 31/198* (2006.01)
*A61K 33/14* (2006.01)
*A23L 1/237* (2006.01)
*C01D 3/06* (2006.01)

(52) U.S. Cl. ................. 424/680; 424/489; 514/561; 426/649; 426/806

(58) Field of Classification Search ................ 424/680, 424/489; 514/561; 426/649, 806
See application file for complete search history.

(56) References Cited

U.S. PATENT DOCUMENTS 3,985,801 A * 10/1976 Thunberg et al. ........... 562/554

OTHER PUBLICATIONS

Fenimore, C.P. et al., "The mutual habit modification of sodium chloride and dipolar ions," Journal of the American Chemical Society, vol. 71, pp. 2714-2717 (1949).*

* cited by examiner

*Primary Examiner*—John Pak
(74) *Attorney, Agent, or Firm*—Merchant & Gould P.C.

(57) ABSTRACT

The present invention relates to a simple, economical, and efficient cyclic process for producing rhombic dodecahedron shaped glycine enriched, free flowing common salt from brine, said process comprising steps of adding glycine of concentration ranging between 10 to 25% to the saturated brine, evaporating the saturated brine containing glycine to obtain crystals having high content of glycine, with mother liquor, washing the crystals with saturated brine to obtain rhombic dodecahedron shaped glycine enriched common salt having glycine content ranging between 0.5 to 1.0% and a washed brine, combining the mother liquor and the washed brine to obtain resulting brine, subjecting the resultant brine to solar evaporation, and repeating the steps of (iii) to (v) to obtain rhombic dodecahedron shaped glycine enriched common salt from brine with glycine concentration ranging between 0.5 to 1.0%.

13 Claims, No Drawings

PROCESS FOR THE PRODUCTION OF GLYCINE ENRICHED NACI CRYSTALS WITH IMPROVED FLOW

FIELD OF THE INVENTION

The present invention relates to a simple, economical, and efficient cyclic process for producing rhombic dodecahedron shaped glycine enriched, free flowing common salt from brine.

BACKGROUND AND PRIOR ART REFERENCES OF THE INVENTION

Interest in crystallization, and in various ways for altering the shapes and structures of crystals, has a long history because an extraordinary range of physical and chemical properties of crystalline solid-state materials is dictated by their crystal form and size. Efforts to modify crystallization processes so as to generate new crystalline forms of substances continue to be of considerable importance for various reasons including, for example, improvement of mass-handling characteristics of particulate materials, production of materials that are stronger or more durable than existing materials, production of materials having improved physical characteristics such as optical clarity, production of materials with long storage period, production of crystalline substance with better flow characteristics, etc.

Conventional ways of altering the shape (i.e., the "habit") or the crystal lattice (i.e., the "morphology") of a crystalline material include: (1) using additives (Weissbuch et al., Science 253:637, 1991; Addadi et al., Topics in Stereochem. 16:1, 1986; Addadi et al., Angew. Chem. Int. Ed. Engl. 24:466, 1985; and Addadi et al., Nature 296:21, 1982); (2) changing the crystallization solvent (including crystallization from the gas phase) used to dissolve the crystallization solute; (3) changing supersaturation of the crystallizing solution; (4) and altering the rate of evaporation.

Common salt, apart from being an essential dietary component, is a basic raw material for the manufacture of a wide variety of industrial chemicals viz, sodium carbonate (soda ash), sodium hydroxide (caustic soda), and chlorine. Besides, salt is used in textile, dairy, dyeing, food, fertilizer, paper and pharmaceutical industries. Caking of water-soluble inorganic salt such as common salt is a common storage problem. Caking is believed to occur in such salt because of the formation of solid inter-crystallin bridges that cement crystals together. Evaporation of minute amount of water on the surface of the crystals causes the formation of inter-crystalline bridges and consequently caking over the period of storage time. Understandably, caking reduces free-flow properties of common salt that has got direct negative influence in its use as dietary component and increases storage problem. Besides salt bridge formation, shape of the crystalline particles has got direct influence on the free-flow property of the substance. Larger inter-crystalline surface area contacts, as it is in cubic form, has negative influence on the free-flow properties. Obviously, the inter-crystalline surface contact area is greatly reduced in case of spherical or near spherical crystallites and thereby increasing its free-flow property.

In the prior art (R. Kern, 1953, Compt. Rend., 23b, 830), it is shown that supersaturation has definite effect on the modification of crystal habit of common salt. At a high supersaturation, common salt crystals grow as octahedron ((111) faces) shaped crystals instead of its normal cubic ((100) faces) form. However, these conditions are too extreme to be of any practical use in production of modified crystals of common salts.

In the prior art, Urea is known to modify common salt crystals from cubic to octahedron since 1783 (J. B. L Rome de l'Isle, 1783, Crystallographie, 2, Ed. Paris). However, because of its toxicity, urea cannot be used as habit modifier of common salt for dietary application.

In the prior art (Brit. Patent No. 752, 582, by N. V. Koninklijke Nederlandsche Zoutindustre, 1954), it is claimed that small amount of potassium ferrocyanide (4 ppm by weight) inhibits caking of common salt to a considerable extent. The plausible explanation of the efficiency of potassium ferrocyanide as anti-caking agent is that the habit modifier causes the inter-crystalline caking bridges to become dendritic and therefore friable. Although it finds application where common salts have to be dispersed over a large area such as in de-icing applications in winter, it cannot be used as dietary component because of the possible toxicity of the cyanide compounds.

In the prior art, (L. Phoenix, British Chemical Engineering, Vol-11, 1966, 34), a long list of various habit modifiers and their effectiveness as anti caking agent has been reported. This list includes cyanide salts of various metal ions, cadmium chloride, lead chloride, potassium silico-tungstate, ammonia triacetamide, victamide etc. These agents at low concentrations modify the habit of NaCl crystals from cubic (100) to dendrites of (100) and octahedron. (111) forms. However, none of these additives may be used in NaCl as dietary product due to possible toxicity of the additives and other practical difficulties.

In the prior art, (Scrutton, A. New Sci. Group, Imp. Chem. Ind. PLC, Runcorn, UK. Symposium Papers—Institution of Chemical Engineers, North Western Branch (1985), (3, Cryst. Habit), 3.1–3.13.), it is shown that NaOH can also act as habit modifier of NaCl in an evaporative crystallizer leading to octahedral (111) shaped NaCl crystals. Obviously, both crystallization technique (i.e. evaporative crystallization) and corrosive nature of NaOH habit modifier do not offer any potential to develop a method for generating modified NaCl crystals for dietary application.

In the prior art, (Sasaki, Shigeko; Yokota, Masaaki; Kubota, Noriaki. Iwate Univ., Morioka, Japan. Nippon Kaisui Gakkaishi (2001), 55(5), 340–342.), it is described that the octahedral {111} faces of NaCl crystal appeared in the presence of citric acid when crystallized at an adjusted pH of 2.72. These new faces were never observed at the natural pH (=0.75) of citric acid. Although, citric acid has good health care property, the disadvantage of this method is the requirement of pH adjustment and the fact that only octahedral crystals—which are less spherical in nature compared to dodecahedral crystals of the present invention—are obtained.

In the prior art, (Fenimore, Charles P.; Thrailkill, Arthur. J. Am. Chem. Soc. 1949, 71, 2714), it is described that Glycine, pyridine, betaine, and β-alanine in aq. NaCl solutions modify the crystal habit of growing NaCl; the first causes the formation of rhombic dodecahedra, the others give octahedra. The main drawback of the prior art is that, even though rhombic dodecahedra are obtained: with Glycine, the initial concentration of Glycine required is as high as 10% in saturated brine. Moreover, in the course of the crystallization process, the Glycine concentration continues to increase and a sizable amount of Glycine can co-precipitate along with salt after the saturation limit of Glycine is attained. This would make the process uneconomical and render the salt unacceptable.

The prior art neither points out this weakness nor any solution. Theoretical considerations (A. Julg and B. Deprick, J. Cryst. Growth., 1993, 62, 587; B. Deprick-Cote, J. Langlet, J. Caillet, J. Berges, E. Kassab and R. Constanciel, Theor. Chim. Acta., 1992, 82, 435) suggest that the zwitterionic form of Glycine is getting adsorbed on (110) planes of NaCl and thereby making this face to grow more slowly compared to (100) planes resulting into the formation of rhombic dodecahedron crystals. Glycine is more attractive as habit modifier as it helps develop the (110) faces resulting in rhombic dodecahedron (i.e. nearly spherical) shaped NaCl crystals.

According to Ullmann's Encyclopedia. (2002), Glycine is reported to have a refreshing, sweetish flavor, and occurs abundantly in mussels and prawns. It is considered to be an important flavor component of these products. When used as an additive for vinegar, pickles, and mayonnaise, it attenuates the sour taste and lends a note of sweetness to their aroma. In other prior art [Pillsbury Comp., U.S. Pat. No. 3,510,310, 1970 and C. Colburn, *Am. Soft Drink J.* 126 (1971)] Glycine is reported to be used to mask the aftertaste of the sweetener saccharin. Glycine is also reported to exhibits a special preservative effect [A. G. Castellani, *Appl. Microbiol.* 1 (1953) 195. Nisshin Flour Milling, JP 7319945, 1973(G. Ogawa, K. Taguchi); *Chem. Abstr.* 81 (1974) 76689z. Nippon Kayaku, JP-Kokai 81109580, 1981; *Chem Abstr.* 95 (1981) 202313b]. The above prior art clearly indicates that not only is Glycine not harmful in any way, it may in fact impart a beneficial effect to certain foods. In the present invention such foods would be those where salt is used and which contains 0.5–1.0% Glycine as additive.

OBJECTS OF THE PRESENT INVENTION

The main object of the sent invention is to develop a simple, economical, and efficient cyclic process for producing rhombic dodecahedron shaped glycine enriched, free flowing common salt from brine.

Yet another object of the present invention is to develop process wherein the brine can be taken from all possible sources.

Still another object of the present invention is to develop a process wherein the drying is at room temperature to make is cost effective.

Still another object of the invention is to develop a process wherein the co-crystallised Glycine can be largely removed from the salt by washing with saturated brine.

Still another object of the present invention is to overcome the difficulty in the use of Glycine as crystal habit modifier of salt as revealed in the prior art and to provide a practical process to generate near spherical (rhombic dodecahedron) crystallites of NaCl using Glycine as habit modifier.

Another objective is to show that Glycine can be dissolved up to the required quantity in both artificial and natural brines to effect the desired habit modification during solar salt production.

Another objective is to show that the crystal habit modification is best effected when the temperature of brine during evaporation is less than 40° C. making it ideally suited for solar salt production.

Yet another objective is to devise a simple means of removing excess quantities of Glycine that simultaneously crystallize with salt during the evaporation process.

Another objective is to show that the habit modification property of Glycine is retained in real brine systems that contain other dissolved salts.

Another objective is to use saturated brine for washing the habit modified salt crystals in order to dissolve the Glycine in the saturated brine without loss of salt.

Another objective is to adjust the quantity of saturated brine taken for washing of the habit modified salt as described in 5 above in a manner so as to obtain saturated brine with required concentration of Glycine for direct re-use.

Another objective is to show that during washing of habit-modified salt with saturated brine as described in 5 above there is no alteration in the crystal morphology of the salt.

Another objective is to show that the salt obtained has superior flow characteristics when compared with the salt produced under similar conditions without the use of Glycine.

Yet another objective is to provide between 0.5–1.0% Glycine in the habit modified salt for purposes where Glycine is reported to have a beneficial effect as micronutrient, flavorant or preservative.

Another objective is to produce habit modified salt from the the Glycine-containing sated brine obtained after washing of the habit modified salt.

Another objective is to eliminate loss of Glycine except to the extent as desired for obtaining a Glycine-fortified salt to make the process practically useful.

SUMMARY OF THE PRESENT INVENTION

The present invention relates to a simple, economical, and efficient cyclic process for producing rhombic dodecahedron shaped glycine enriched, free flowing common salt from brine, said process comprising steps of adding glycine of concentration ranging between 10 to 25% to the saturated brine, evaporating the saturated brine containing glycine to obtain crystals having high content of glycine, with another liquor, washing the crystals with saturated brine to obtain rhombic dodecahedron shaped glycine enriched common salt having glycine content ranging between 0.5 to 1.0% and a washed brine, combining the mother liquor and the washed brine to obtain resulting brine, subjecting the resultant brine to solar evaporation, and repeating the steps of (iii) to (v) to obtain rhombic dodecahedron shaped glycine enriched common salt from brine with glycine concentration ranging between 0.5 to 1.0%.

DETAILED DESCRIPTION OF THE PRESENT INVENTION

Accordingly, the present invention relates to a simple, economical, and efficient cyclic process for producing rhombic dodecahedron shaped glycine enriched, free flowing common salt from brine, said process comprising steps of adding glycine of concentration ranging between 10 to 25% to the saturated brine, evaporating the saturated brine containing glycine to obtain crystals having high content of glycine, with mother liquor, washing the crystals with saturated brine to obtain rhombic dodecahedron shaped glycine enriched common salt having glycine content ranging between 0.5 to 1.0% and a washed brine, combining the mother liquor and the washed brine to obtain resulting brine, subjecting the resultant brine to solar evaporation, and repeating the steps of (iii) to (v) to obtain rhombic dodecahedron shaped glycine enrich common salt from brine with glycine concentration ranging between 0.5 to 1.0%.

In an embodiment of the present invention, wherein a simple, economical, and efficient cyclic process for producing rhombic dodecahedron shaped glycine enriched, free flowing common salt from brine, said process comprising steps of:
  adding glycine of concentration ranging between 10 to 25% to the saturated brine,
  evaporating the saturated brine containing glycine to obtain crystals having high content of glycine, with mother liquor,
  washing the crystals with saturated brine to obtain rhombic dodecahedron shaped glycine enriched common salt having glycine content ranging between 0.5 to 1.0% and a washed brine, combining the mother liquor and the washed brine to obtain resulting brine,
  subjecting the resultant brine to solar evaporation, and
  repeating the steps of (iii) to (v) to obtain rhombic dodecahedron shaped glycine enriched common salt from brine with glycine concentration ranging between 0.5 to 1.0%.

In still another embodiment of the present invention, wherein the brine is selected from a group comprising synthetic brines, natural brines including sea-, sub-soil and lake brines.

In still another embodiment of the present invention, wherein evaporation is conducted in the temperature range of 20–40° C. and more preferably solar evaporation under ambient condition.

In still another embodiment of the present invention, wherein the initial concentration of Glycine in saturated brine is maintained in the range 22–25% (w/v).

In still another embodiment of the present invention, wherein co-crystallised Glycine can be largely removed from the salt by washing with saturated brine.

In still another embodiment of the present invention, wherein the volume of saturated brine taken for washing is such that the Glycine content of the brine becomes 22–25% after washing.

In still another embodiment of the present invention, wherein the washings can be directly subjected to solar evaporation to once again produce habit modified salt or combined with the mother liquor remaining after salt preparation and then subjected to solar evaporation.

In still another embodiment of the present invention, wherein washing of the salt with sated brine has no deleterious effect on the morphology of the habit modified salt.

In still another embodiment of the present invention, wherein the habit-modified salt has improved flow characteristics because of its near spherical shape.

In still another embodiment of the present invention, wherein the habit modified salt has lesser tendency to stick to the surface of plastic.

In still another embodiment of the present invention, wherein the glycine utilization efficacy is ranging between 95 to 100%.

In still another embodiment of the present invention, wherein the glycine in the salt can serve as flavorant, preservative and micronutrient as reported in the prior art on the properties of Glycine.

In still another embodiment of the present invention, wherein A method for producing Glycine-fortified common salt wherein the Glycine serves the additional function of being a habit modifier to produce near spherical crystals with improved flow characteristics is reported. The Glycine is recycled in the method of the invention for practicality. The invention is applicable to salt production from both synthetic and natural brines and especially suitable for solar salt production.

The present invention relates to a method for recycling Glycine in the process for generating near spherical crystals of NaCl enriched with Glycine micronutrient. The present process deals with the recrystallization of commercially available common salt crystals under ambient conditions in presence of Glycine (crystal habit modifier) to produce rhombic dodecahedron crystals with superior free-flow property instead of the normal cubic form. The Glycine habit modifier is continuously recycled while retaining 0.5–1.0% (w/w) of Glycine in the salt to serve as micronutrient. The process can be applied to pure brine solutions or is even amenable to natural brine systems such as sea brine and subsoil brine.

The present invention seeks to obviate the apparent difficulties in utilising the crystal habit modifying characteristics of glycine, namely, the requirement for high concentrations of glycine for effective habit modification and the problem of high amounts of Glycine in the crystallized salt which was not reported in the prior art but became evident in the course of the present invention. The process as reported in the prior art is practically unviable both in terms of high usage level of Glycine and also in terms of too high a level of Glycine in habit modified salt which can affect the taste and suitability of the salt. The main inventive steps of the present invention are: the realisation that substantial quantities of Glycine are lost in the salt during the evaporation process, (ii) the realisation that Glycine can be washed off from crystal habit modified salt using saturated brine without any loss of salt and retaining the desired morphology of the salt crystal, (iii) the further realisation that the brine obtained after washing the salt contains Glycine in the desired amount and can therefore be solar evaporated to directly obtain habit modified salt without the need for any additional Glycine. A further inventive step is the generation of twin benefits from the use of Glycine as additive in brine, namely the crystal habit modifying property that imparts free flow characteristics due to the near-spherical shape of the salt and its potential use as a flavorant, preservative and micronutrient in the salt.

In an embodiment of the present invention the brine used for production of habit modified salt can either be synthetic brine obtained by dissolving salt or brine of natural origin such as sea-, sub-soil and lake brines.

In another embodiment of the present invention, Glycine is added into saturated brine to a concentration of 22–25% (w/v) to ensure dodecahedron form of salt crystals form inception of crystallisation.

In another embodiment of the present invention the temperature of brine is maintained at less than 40° C. and evaporation was conducted under ambient conditions.

In another embodiment of the present invention the volume of saturated brine taken was in the range of 100-500 ml and the brine was evaporated to 10–20% of the original volume.

In yet another embodiment of the present invention the mother liquor is decanted and the crystallised salt is washed with fresh saturated brine not containing Glycine.

In yet another embodiment of the present invention the volume of saturated brine taken for washing is such that the Glycine content in the washing is restored to the original 22–25% (w/v) after addition of the mother liquor from salt crystallisation into the washing.

In yet another embodiment of the present invention the salt retains its habit modified form after washing with fresh saturated brine.

In yet another embodiment of the present invention the habit modified salt is distinctly more free flowing in nature than salt produced without Glycine during the crystallisation process under otherwise identical conditions.

In yet another embodiment of the present invention the Glycine residue in salt is in the range of 0.5–1.0% w/w.

In yet another embodiment of the present invention the Glycine utilisation efficiency is between 95–100%.

The following examples are given by way of illustration and should not be construed to limit the scope of the invention.

EXAMPLE 1

Excess amount of commercially available NaCl was added to 150 ml of distilled water and the mixture was stirred at room temperature for 0.5 h. The solid/liquid mixture was then filtered and 100 ml of such filtered saturated brine was kept for crystallization in an open beaker under ambient conditions in the laboratory. After 90% evaporation, the resulting crystals were harvested by filtration and drying in a fluidized bed-type of drier. Microscopic observation revealed that the crystals were of cubic form.

EXAMPLE 2

Saturated brine was prepared as in 1 above. 10 g of commercially available Glycine was added into 100 ml of brine and stirred at room temperature. The resulting solution containing 10% (w/v) Glycine in saturated brine was evaporated under otherwise identical condition as in 1 above and the crystals were isolated by filtration and dried in a fluidized bed type of drier. The crystals obtained were largely of cubic and octadecahedron forms.

EXAMPLE 3

The experiment of Example 2 was repeated with 15% initial Glycine concentration instead of 10%. The crystals of NaCl were mainly of octadecahedron shape. Some Glycine crystals were also observed.

EXAMPLE 4

The experiment of Example 2 was repeated with 25% initial Glycine concentration instead of 10%. The crystals of NaCl were mainly of rhombic dodecahedron shape. Significant amount of Glycine crystals were also found to be crystallized with NaCl. The flow properties of the salt crystals were compared qualitatively with that of the salt of Example 1 above and the former were found to be distinctly more free-flowing. The salt also had much lesser tendency to stick to the surface of the plastic container in which it was stored.

EXAMPLE 5

The experiment of Example 4 was repeated except that evaporation was carried out at 50° C. instead of under ambient condition. The resulting salt crystals were found to be of cubic form and of similar shape as that described in Example 1. Glycine crystals were also present in the salt.

EXAMPLE 6

The crystals obtained in Example 4 were washed with 90 ml of saturated brine prepared as in Example 1 above. After washing, the resulting crystals were isolated and dried as described in Example 1. Observation of such crystals revealed that the crystals of salt retained the rhombic dodecahedron morphology but most of the Glycine crystals had disappeared. IR analysis of the salt using a quantitative calibration technique indicated that its Glycine content to be 0.83% (w/w).

EXAMPLE 7

The mother liquor obtained in Example 4 was combined with the washings of Example 6 and left for evaporation under ambient condition. Glycine recycling efficiency of 95–99% is disclosed. Crystals were then harvested and dried. The salt crystals were found to be rhombic dodecahedron in shape and contained significant quantities of Glycine crystals in a manner identical to the salt described in Example 4. This process of recycling the mother liquor and washings was repeated seven times and each time the salt crystals were found to be rhombic dodecahedron in shape, with 0.5–1.0 Glycine content.

EXAMPLE 8

The experiment of Example 4 was rob with 500 mL of sub-soil brine instead of pure brine. The specific gravity of the brine was 1.208 kg/L. The brine was evaporated up to a specific gravity of 1.239 kg/L. The resulting crystals of salt were of rhombic dodecahedron shape with significant quantities of co-crystallised Glycine crystals. The salt was washed with fresh 1.208 kg/L sub-soil brine and the crystal morphology was found to be retained while the Glycine crystals were found to have largely disappeared.

The Main Advantages of the Present Invention are:
1. A process for generating Glycine-enriched salt with improved flow characteristics due to the near spherical nature of the crystals.
2. Use of permissible additive as crystal habit modifier.
3. Versatility of the process in as much as impurities in natural brine have no adverse effect on the crystal habit modification that leads to improved flow characteristics.
4. Amenable to production of salt through solar evaporation.
5. Near quantitative recycle of Glycine for practicality.

The invention claimed is:
1. A process for producing salt comprising:
 (i) adding glycine to a first saturated brine to achieve a glycine concentration of 22 to 25% (w/v),
 (ii) evaporating the first saturated brine and glycine to obtain:
  crystals comprising a high content of glycine, and mother liquor;
 (iii) washing the crystals with a second saturated brine to obtain:
  rhombic dodecahedron shaped salt comprising 0.5 to 1.0% glycine, and
  a wash brine.
2. A process as claimed in claim 1, wherein the first saturated brine or second saturated brine comprises synthetic brine or natural brine.
3. A process as claimed in claim 1, wherein evaporating the first saturated brine and glycine comprises evaporating at 20–40° C.
4. A process as claimed in claim 1, wherein washing with the second saturated brine removes glycine crystals.
5. A process as claimed in claim 1, the process further comprising subjecting the wash brine to solar evaporation.

6. A process as claimed in claim 1, wherein washing of the crystals with the second saturated brine has no deleterious effect on the morphology of the rhombic dodecahedron shaped salt.

7. A process as claimed in claim 1, wherein the rhombic dodecahedron shaped salt has improved flow characteristics because of its near spherical shape.

8. A process as claimed in claim 1, wherein the rhombic dodecahedron shaped salt has lesser tendency to stick to the surface of plastic than salts that do not have rhombic dodecahedron shaped crystals.

9. A process as claimed in claim 1, wherein the glycine recycling efficiency is 95–99%.

10. A process as claimed in claim 1, wherein the glycine in the salt can serve as flavorant, preservative or micronutrient.

11. A process as claimed in claim 1, wherein the brine comprises sea brine, sub-soil brine, or lake brine.

12. A process as claimed in claim 1, wherein evaporation is conducted under ambient condition.

13. A process as claimed in claim 1, the process further comprising:
- (iv) combining the mother liquor and the wash brine to obtain a combined brine,
- (v) subjecting the combined brine to solar evaporation, and
- (vi) repeating the steps of (iii) to (v) to obtain rhombic dodecahedron shaped salt comprising a glycine content ranging between 0.5 to 1.0 wt %.

* * * * *